United States Patent
Sasaki

(10) Patent No.: US 9,830,021 B2
(45) Date of Patent: Nov. 28, 2017

(54) IMAGE DISPLAY APPARATUS THAT IRRADIATES LIGHT TO AN OBJECT PLACED THEREON AND DISPLAYS A GRAPHICAL USER INTERFACE AND CONTROL METHOD THEREFOR

(71) Applicant: CANON KABUSHIKI KAISHA, Tokyo (JP)

(72) Inventor: Masatsugu Sasaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/619,793

(22) Filed: Feb. 11, 2015

(65) Prior Publication Data
US 2015/0234540 A1    Aug. 20, 2015

(30) Foreign Application Priority Data

Feb. 14, 2014 (JP) ................................. 2014-026811

(51) Int. Cl.
*G06F 3/042* (2006.01)
*G06F 3/0482* (2013.01)
(52) U.S. Cl.
CPC .......... *G06F 3/0421* (2013.01); *G06F 3/0482* (2013.01); *G06F 2203/04109* (2013.01)
(58) Field of Classification Search
CPC ......... G06F 3/0421; G06F 2203/04109; G06F 3/048; G06F 3/0482
USPC ....................................................... 345/175
See application file for complete search history.

(56) References Cited

U.S. PATENT DOCUMENTS

| 4,004,360 | A | * | 1/1977 | Hammond | .............. | G09F 13/10 |
| | | | | | | 362/218 |
| 4,510,708 | A | * | 4/1985 | Pokrinchak | .......... | G02B 27/024 |
| | | | | | | 40/361 |
| 4,908,876 | A | * | 3/1990 | DeForest | ............. | G02B 27/026 |
| | | | | | | 349/17 |
| 5,430,964 | A | * | 7/1995 | Inbar | .................... | G02B 27/024 |
| | | | | | | 40/361 |

(Continued)

FOREIGN PATENT DOCUMENTS

| JP | 02-013920 A | 1/1990 |
| JP | 2000-241749 A | 9/2000 |
| JP | 2008-058519 A | 3/2008 |

OTHER PUBLICATIONS

The above patent documents were cited in a European Search Report issued on Jul. 13, 2015, which is enclosed, that issued in the corresponding European Patent Application No. 15154903.7.

*Primary Examiner* — Julie Anne Watko
(74) *Attorney, Agent, or Firm* — Cowan, Liebowitz & Latman, P.C.

(57) ABSTRACT

Provided is an image-display apparatus on which an object to be observed can be applied, the image-display apparatus comprising: a display screen; a plurality of light-emitting units arranged to emit light out of the screen from behind the screen; a plurality of light sensors arranged behind the screen to detect light including light emitted from at least one light-emitting unit and reflected from an object applied to the display screen, and to output at least first and second detection values; and a determination unit configured to determine, based on the detection values output by the plurality of sensors, a first region of the display screen corresponding to a region to which the object is applied to the display screen.

19 Claims, 18 Drawing Sheets

(56) References Cited

U.S. PATENT DOCUMENTS

| | | | |
|---|---|---|---|
| 5,491,332 A * | 2/1996 | Inbar | G06F 3/0425 250/221 |
| 5,835,173 A * | 11/1998 | Inbar | G02B 27/026 345/102 |
| 5,890,305 A | 4/1999 | Inbar et al. | |
| 6,101,749 A * | 8/2000 | Inbar | G02B 27/024 345/90 |
| 6,311,419 B1 | 11/2001 | Inbar | |
| 9,262,015 B2 * | 2/2016 | Avrahami | G06F 1/1626 |
| 2010/0066667 A1 * | 3/2010 | MacDougall | G06K 9/00228 345/156 |
| 2010/0218249 A1 * | 8/2010 | Wilson | H04L 9/3226 726/19 |
| 2013/0285987 A1 * | 10/2013 | Ilmonen | G06F 3/0425 345/175 |

* cited by examiner

FILM-SIZE DETERMINATION TABLE

| STANDARDS | SIZE (VERTICAL SIZE X TRANSVERSE SIZE) |
|---|---|
| CUTTING IN HALF | 356 x 432mm |
| BIG SQUARE | 356 x 356mm |
| BIG QUARTER | 279 x 356mm |
| QUARTER | 254 x 305mm |
| CUTTING INTO SIX PARTS | 203 x 254mm |
| CUTTING INTO EIGHT PARTS | 165 x 216mm |

*Fig.3*

| ID:1 | | | | | | | ID: m |
|---|---|---|---|---|---|---|---|
| 2955 | 2956 | 2955 | 2955 | 2955 | 2955 | 2956 | |
| 2956 | ... | ... | 2955 | 2956 | 2956 | 2955 | ID: n |
| ... | ... | ... | 2956 | 2955 | 2956 | 2956 | |
| ... | ... | ... | 2955 | 2956 | 2955 | 2955 | |
| ... | ... | 2955 | ... | ... | ... | ... | |
| ... | ... | ... | ... | ... | ... | ... | |
| ... | ... | ... | ... | ... | ... | ... | |
| ... | ... | ... | ... | ... | ... | ... | |
| ... | ... | ... | ... | ... | ... | ... | |
| ... | ... | ... | ... | ... | ... | 2954 | ID: z |

ID:m+1 (second row label)

*Fig.9A*

| ID:1 | | | | | | | ID: m |
|---|---|---|---|---|---|---|---|
| 2955 | 2956 | 2955 | 2955 | 2961 | 2960 | 2960 | |
| 2956 | ... | ... | 2956 | 2960 | 2961 | 2962 | ID: n |
| ... | ... | ... | 2958 | 2962 | 2960 | 2960 | |
| ... | ... | ... | 2955 | 2957 | 2955 | 2957 | |
| ... | ... | 2957 | ... | ... | ... | ... | |
| ... | ... | ... | ... | ... | ... | ... | |
| ... | ... | ... | ... | ... | ... | ... | |
| ... | ... | ... | ... | ... | ... | ... | |
| ... | ... | ... | ... | ... | ... | ... | |
| ... | ... | ... | ... | ... | ... | 2954 | ID: z |

ID:m+1 (second row label)

*Fig.9B*

|   |   | R1 | R2 |   |   | R |
|---|---|---|---|---|---|---|
| 0 | 0 | 0 | 0 | 6 | 5 | 4 |
| 0 | ... | ... | 1 | 4 | 5 | 7 |
| ... | ... | ... | 2 | 7 | 4 | 4 |
| ... | ... | ... | 0 | 1 | 0 | 2 |
| ... | ... | 2 | ... | ... | ... | ... |
| ... | ... | ... | ... | ... | ... | ... |
| ... | ... | ... | ... | ... | ... | ... |
| ... | ... | ... | ... | ... | ... | ... |
| ... | ... | ... | ... | ... | ... | ... |
| ... | ... | ... | ... | ... | ... | 0 |

*Fig.11*

IMAGE DISPLAY APPARATUS THAT IRRADIATES LIGHT TO AN OBJECT PLACED THEREON AND DISPLAYS A GRAPHICAL USER INTERFACE AND CONTROL METHOD THEREFOR

BACKGROUND OF THE INVENTION

Field of the Invention

The present invention relates to an image display apparatus and a control method therefor.

Description of the Related Art

Heretofore, when X ray films obtained by photographing with X rays or the like were interpreted, the films were placed on a film viewer to be interpreted. Recently, with the digitalization of medical images, a monitoring diagnosis using an image display apparatus (medical viewer) has become mainstream, and some medical institutions do not possess a film viewer, as the filmless operation becomes more popular. Additionally, medical image display apparatuses having a function of using the (digital) display apparatus body as a film viewer by making a backlight emit light with high brightness and performing white display on a liquid crystal panel are beginning to be widely used. By using such a medical image display apparatus, not only the interpretation of digital images but also the interpretation of film images is possible with a single medical image display apparatus, which improves the convenience. On the other hand, there has been a problem, even since the age of film interpretation using a film viewer, in that a region where light is emitted with high brightness (hereinafter referred to as a film viewer region) is larger than the area of the film, potentially causing glare or otherwise affecting the viewer, whereby an erroneous diagnosis is caused or interpretation efficiency is lowered. This problem exists also in medical image display apparatuses having a film viewer function.

Japanese Patent Application Laid-open No. H2-13920 discloses a technology of measuring the quantity of light that enters from the outside of an image display apparatus, while mechanically vertically moving a linear photosensor provided in the apparatus, to determine a region (film region) where a film is placed, and matching an emission area with the film region. Additionally, Japanese Patent Application Laid-open No. 2000-241749 discloses a technology of detecting a film region by sandwiching a pressure sensor and a film in a clip member, or a technology of detecting a film region by pressing four corners of a film that is set in a monitor by using a touch panel.

SUMMARY OF THE INVENTION

In the above Japanese Patent Application Laid-open No. H2-13920, it is possible to detect the film region by monitoring the quantity of the light that enters from the outside of the apparatus in a bright environment. However, there is a possibility that sufficient difference between the light quantity of the film region and the light quantity of the region outside the film is not present in a dark environment in which little light enters from the outside of the apparatus, such as a room for radiographic interpretation. In such a case, the film region may be erroneously detected.

In Japanese Patent Application Laid-open No. 2000-241749, it is possible to detect the film region regardless of the brightness of the radiograph interpretation environment by placing the film on the monitor and pressing the film region to designate the film. However, there is a possibility that a finger directly presses the monitor, and therefore a fingerprint is sometimes adhered to a monitor surface and influences a diagnosis. Furthermore, in the technologies described in the above two patent documents, there is a possibility that a dedicated linear sensor or touch panel needs to be provided in the image display apparatus, and this causes an increase in size of a circuit or an increase in cost.

Therefore, in the present invention, in an image display apparatus capable of using a part of a screen as lighting when viewing through an object to be interpreted such as a film, and performing observation, the region on which the object to be interpreted is fixed is accurately detected.

A first aspect of the present invention is an image-display apparatus on which an object to be observed can be applied, the image-display apparatus comprising:

a display screen;

a plurality of light-emitting units arranged to emit light out of the screen from behind the screen;

a plurality of light sensors arranged behind the screen to detect light including light emitted from at least one light-emitting unit and reflected from an object applied to the display screen, and to output at least first and second detection values; and a determination unit configured to determine, based on the detection values output by the plurality of sensors, a first region of the display screen corresponding to a region to which the object is applied to the display screen.

A second aspect of the present invention is a control method for an image-display apparatus on which an object to be observed can be applied, the image-display apparatus comprising:

a display screen;

a plurality of light-emitting units arranged to emit light out of the screen from behind the screen; and a plurality of light sensors arranged behind the screen to detect light including light emitted from at least one light-emitting unit and reflected from an object applied to the display screen, and to output at least first and second detection values;

the control method comprising:

lighting the display screen with at least one light-emitting unit;

detecting light received by the plurality of light sensors;

each light sensor outputting a first detection value when the image-display apparatus does not have an object applied to it and a second detection value when the image-display apparatus does have an object applied to it;

receiving detection values from each sensor;

determining an object region on the display screen on the basis of the first and second detection values; and causing at least one light-emitting unit in the object region to emit light with a greater brightness than other regions.

According to the present invention, in an image display apparatus capable of using a part of a screen as lighting when viewing through an object to be interpreted such as a film, and performing observation, it is possible accurately to detect the region of the screen on which the object to be interpreted is fixed. Further features of the present invention will become apparent from the following description of exemplary embodiments with reference to the attached drawings.

BRIEF DESCRIPTION OF THE DRAWINGS

FIG. 3 shows an example of a determination table of film size of the first embodiment;

FIGS. 9A and 9B show examples of sensor values in a state in which the film is present and a state in which the film is not present, according to the first embodiment;

FIG. 11 shows Example 2 related to the correction of the film viewer region of the first embodiment;

DESCRIPTION OF THE EMBODIMENTS

First Embodiment

Hereinafter, a medical image display apparatus according to a first embodiment of the present invention will be described with reference to the figures. The medical image display apparatus of the first embodiment is an image display apparatus that includes a display panel which displays an image, backlights (hereinafter referred to as BLs) which serve as a light-emitting unit for irradiating the display panel with light. The medical image display apparatus can display an image on a screen on the basis of image data, and it can use a partial region of the screen as lighting to irradiate an object to be observed (object to be interpreted) fixed on the screen, such as a film (a photographic film or X-ray film, for example). The medical image display apparatus has control modes of the BLs including: a first BL control mode for performing drift/unevenness correction, and a second BL control mode for determining a region (film region) on the screen on which the film is placed. In the first embodiment, the determination of the film region is performed by switching between the first BL control mode and the second BL control mode for every fixed period, and the BLs in the film region are made to emit light with high brightness, so that a part of the screen can be used as a film viewer. Note that a user of the first embodiment indicates an operator of the medical image display apparatus, such as a radiologist (radiograph-interpreting doctor), unless otherwise stated.

Figure 1:
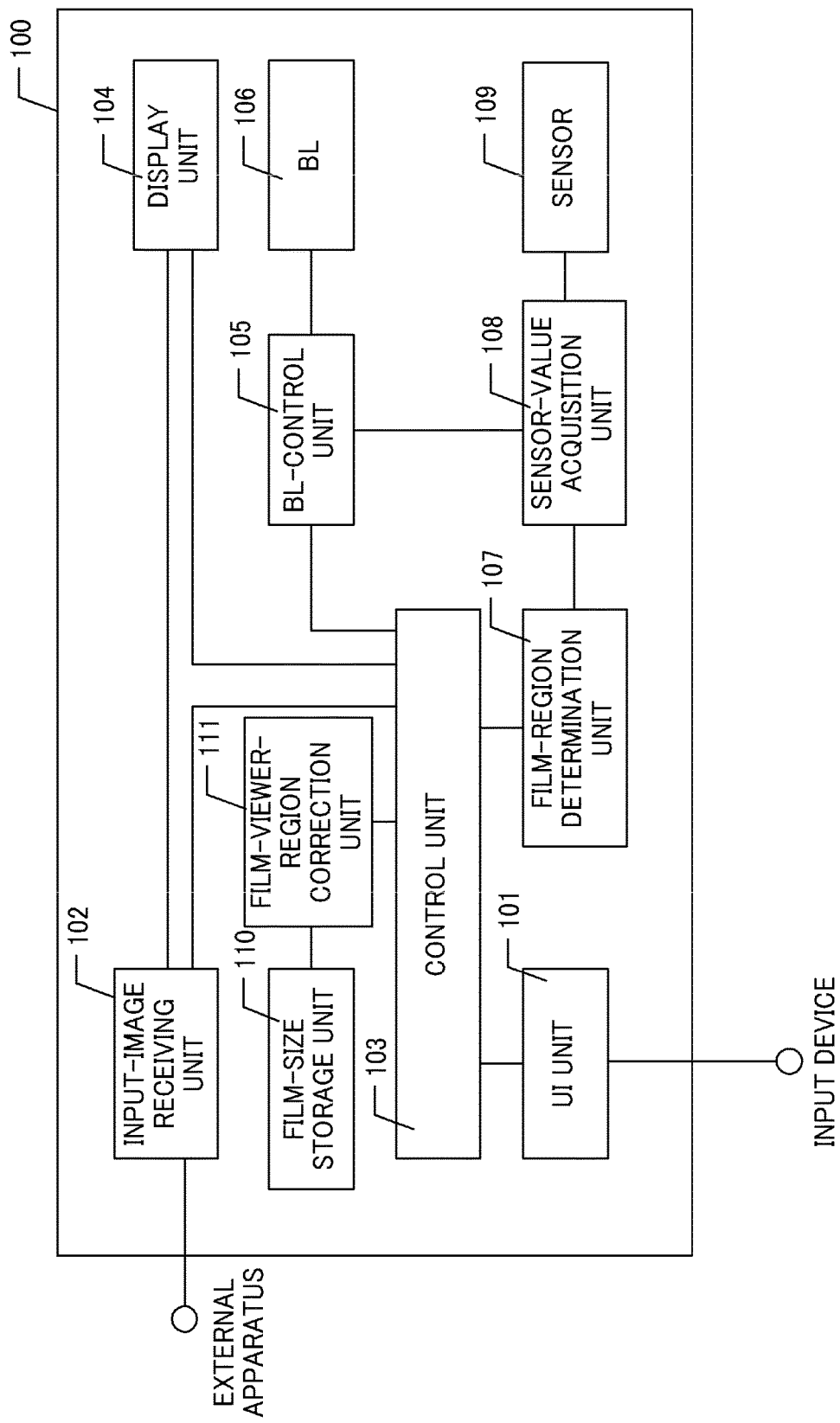
FIG. 1 is a block diagram showing a configuration of a medical image display apparatus of a first embodiment.

FIG. 1 is a block diagram showing a configuration of a medical image display apparatus 100 according to the first embodiment. The medical image display apparatus 100 includes a UI (user interface) unit 101, an input-image receiving unit 102, a control unit 103, a display unit 104, a BL-control unit 105, BLs 106, a film-region-determination unit 107, a sensor-value-acquisition unit 108, and sensors 109. The medical image display apparatus further includes a film size-storage unit 110, and a film-viewer-region-correction unit 111.

The UI unit 101 receives input operation from a user through an input device (such as a mouse or a keyboard) connected to the medical image display apparatus 100, and notifies the control unit 103 of the input operation from the user. For example, in a case where the user performs the designation of "image display", the UI unit 101 notifies the control unit 103 of a digital image to be displayed. The input-image receiving unit 102 outputs image data supplied from an external apparatus (not shown) through an image interface or the like, to the control unit 103 and the display unit 104.

The control unit 103 controls the operation of whole of the medical image display apparatus 100 in accordance with the user operation received from the UI unit 101, and the image data received from the input-image receiving unit 102. Additionally, the control unit 103 may switch each of control modes of the BL-control unit 105, which will be described later, at a fixed interval.

The display unit 104 displays an image based on the image data input from the input-image receiving unit 102, and superimposes a GUI (graphical user interface) image of a menu or the like designated by the control unit 103 on an image based on the above image data, to display the superimposed image. In this embodiment, an example of a case where the display apparatus is a transmission-type liquid crystal display apparatus. However, the display apparatus is not limited to the transmission-type liquid crystal display apparatus. The display apparatus may be any display apparatus that has an independent light source. Additionally, the display apparatus may be a micro-electro-mechanical system (MEMS) shutter system display using a MEMS shutter in place of liquid crystal devices.

The BL-control unit 105 controls BLs 106 in the two modes, namely the first BL control mode for controlling the BLs 106 in order to perform drift/unevenness correction, and the second BL control mode for identifying a film region and making the BLs 106 in the film region emit light with high brightness as the film viewer region. In the first embodiment, although the BL-control unit 105 is shown in a single block, a BL-control unit may be provided for each control mode, and a plurality of BL-control units may be provided. In this case, the control unit 103 switches the BL-control unit, which controls the BLs 106, at a fixed interval.

The BLs 106 are backlights that are arranged on the back surface side of the display unit 104, and irradiate the display unit 104 with light. The BLs 106 are configured by light sources (light-emitting devices) such as light emitting diodes (LEDs). The BLs 106 are configured from a plurality of divided regions where light-emission quantity is individually controlled, the light-emission quantity of each divided region is independently controlled by the BL-control unit 105.

The film-region determination unit 107 acquires values of the sensors 109 through the sensor-value acquisition unit 108 described later. The film-region determination unit 107 identifies a region where a film is placed on the screen of the display unit 104, on the basis of the acquired each sensor value, and notifies the identified regions to the control unit 103. A detailed process performed by the film-region determination unit 107 will be described later. The sensor-value-acquisition unit 108 acquires the respective sensor value from the sensors 109, and notifies the acquired sensor values to the BL-control unit 105 and the film-region-determination unit 107.

Figure 2:
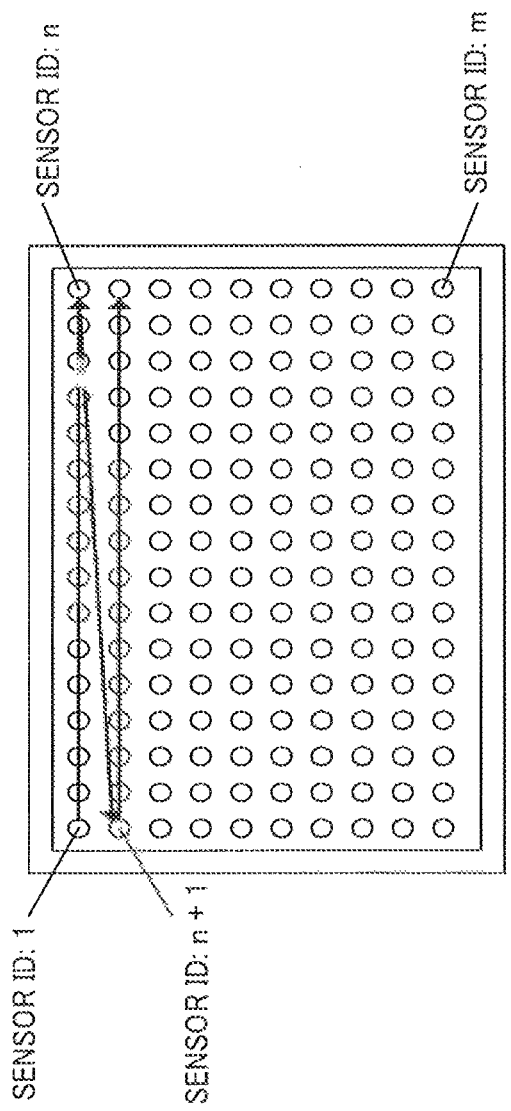
FIG. 2 shows an arrangement example of sensors of the first embodiment.

The sensors 109 are arranged at a plurality of different positions behind the display unit 104 and facing toward the display unit 104 inside the medical image display apparatus 100. The sensors measure the brightness of light incident from the outside of the medical image display apparatus 100 or they measure the brightness of reflected light that is emitted by each of BLs 106 and reflected by the display unit 104. Additionally, each sensor 109 outputs the measured brightness as a sensor value. FIG. 2 shows an arrangement example of the sensors 109. In the first embodiment, description will be hereinafter made assuming that m sensors 109 are present in the medical image display apparatus 100. Additionally, sensor IDs are numbers that are serially assigned to the sensors from a sensor located at an uppermost left position to a sensor located at a lowermost right position.

The film-size-storage unit 110 holds information on typical values of vertical and horizontal size of a film for each film standard as shown in FIG. 3. FIG. 3 shows information on typical values of size of an object to be observed The sizes may be estimated sizes. The film-size-storage unit 110 stores the information in a hard disk or a non-volatile memory that is used as a storage medium.

The film-viewer-region-correction unit 111 corrects the film region identified by the film-region-determination unit 107 on the basis of the film size held by the film-size-storage unit 110, and notifies the control unit 103 of a film region obtained after correction as the film viewer region. Then, the control unit 103 notifies the BL-control unit 105 of information on the film viewer region, and the BL-control unit 105 causes the BLs 106 to emit light on the basis of the information, so that the BLs in the region designated as the film viewer region emit light with high brightness. A detailed process performed by the film-viewer-region correction unit 111 will be described later.

<Description of Processing Flow of Whole of the Invention>

Figure 4:
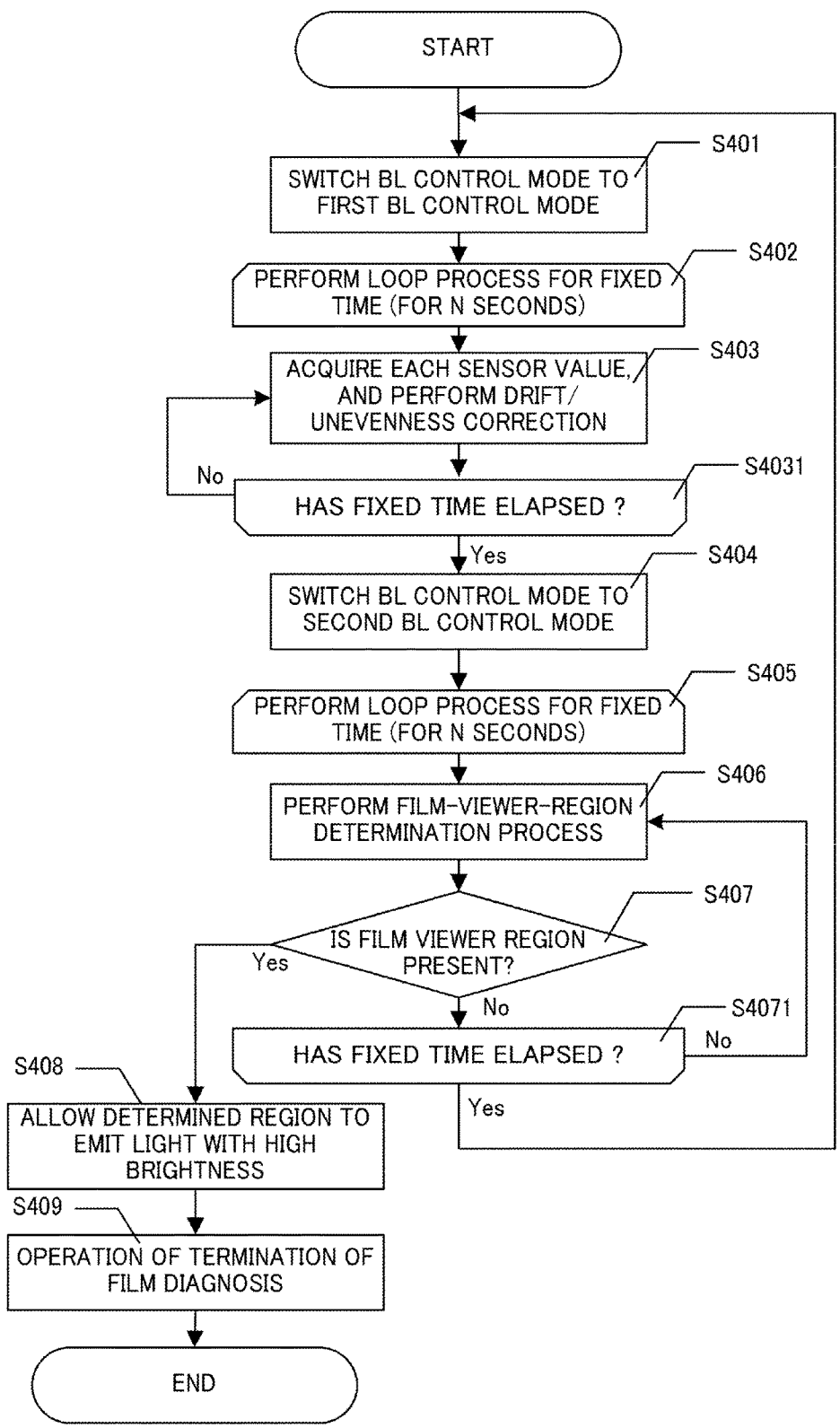
FIG. 4 is an operation flowchart of the medical image display apparatus of the first embodiment.

FIG. 4 is a flow diagram showing whole process according to the first embodiment. When power is supplied and the medical image display apparatus 100 is activated, the medical image display apparatus 100 performs the processes described below.

In Step S401, the control unit 103 notifies the BL-control unit 105 to change (or maintain) the BL control mode to the first BL control mode.

In Step S402, the control unit 103 counts up until a fixed time elapses (e.g., for N seconds) (S4031). When the fixed time elapses (yes in S4031), the process advances to a process of S404. Additionally, a process of S403 is repeatedly performed until the fixed time elapses.

In Step S403, the BL-control unit 105 controls the BLs 106 in the first BL control mode. In the first BL control mode, the BL-control unit 105 acquires respective sensor values of the sensors 109 through the sensor-value acquisition unit 108. The display screen is divided into individually-controllable regions in that each divided region can have its brightness individually controlled. The BL-control unit 105 thus controls the light-emission quantity of the BLs 106 for every divided region so as to limit any unevenness of brightness of the whole of the medical image display apparatus 100 in accordance with each acquired sensor value.

In Step S404, the control unit 103 notifies the BL-control unit 105 to change the BL control mode to the second BL control mode. In the second BL control mode, the control of light-emission quantity for every divided region of the BLs 106, which is controlled in the first BL control mode, is cancelled, and subsequent processes are performed in order to identify the film region.

In Step S405, the control unit 103 counts up the amount of seconds until a fixed time (e.g. N seconds) elapses in S4071. In a case where the fixed time elapses (yes in S4071), the process returns to S401. Additionally, processes of S406 and S407 are repeatedly performed until the fixed time elapses.

In Step S406, the film-region determination unit 107 acquires respective sensor values of the sensors 109 through the sensor-value acquisition unit 108, and determines whether or not a region is present on which the film is placed (hereinafter also known as a film region). In a case where the film region is present, the film-viewer-region-correction unit 111 compares the film region with a film-size-determination table to perform the correction of the film viewer region.

In Step S407, the control unit 103 determines whether or not the film viewer region is present, on the basis of determination results of the film-region determination unit 107 and the film-viewer-region correction unit 111. In a case where the film viewer region is present, the control unit 103 stops counting up the amount of elapsed seconds in S405, and notifies the BL-control unit 105 of a position and size of the film viewer region (corrected film region size). The position of the film viewer region is represented by a coordinate value of, for example, an uppermost left corner of the film viewer region. The BL-control unit 105 performs a process of S408. In a case where the film viewer region is not present and the fixed time has not elapsed, the process returns to S406.

Figure 5:
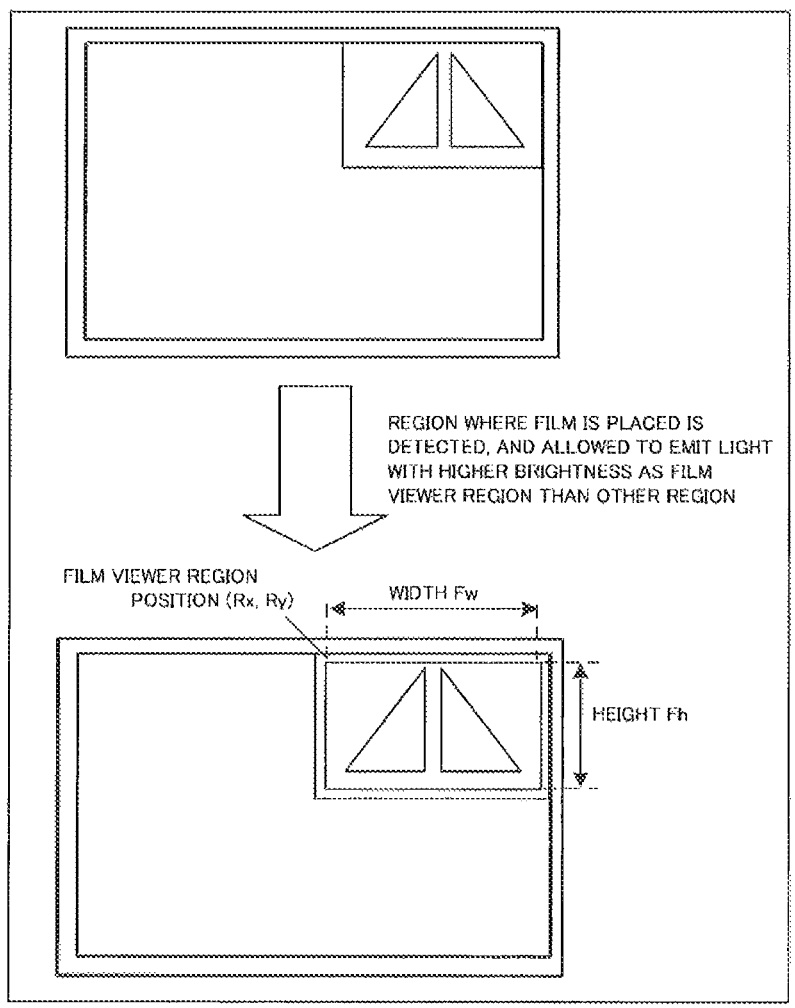
FIG. 5 shows a screen example in which a film viewer region emits light with high brightness, according to the first embodiment.

In Step S408, the BL-control unit 105 allows a divided region of BLs 106 corresponding to the position (Rx, Ry) and the size (width Fw and height Fh) of the film viewer region, which are notified, to emit light with higher brightness compared to other divided regions, as shown in FIG. 5. The divided region where light is emitted with high brightness is determined such that it includes the whole film viewer region. By fixing a film (to the screen) in this state, the user can perform diagnosis of a film image. It is considered that the film viewer region becomes larger than the film region depending on positional relation between the arrangement of the divided region of the BLs 106 and the film region, and light from the backlights leaks around the film. In this case, a black image is displayed in a region of the screen on which the film is not fixed (i.e. a region other than the film viewer region). In other words, the black image is on a part of the display unit 104 corresponding to a region which is not contained in the film viewer region from among the divided regions, the film viewer region being a region in which light is emitted with high brightness, and light leakage (from around the sides of the film) may be suppressed.

In Step S409, in a case in which the user performs a film-diagnosis termination operation, the control unit 103 notifies the BL-control unit 105 of the film-diagnosis termination, and the BL-control unit 105 terminates the control of the BLs 106 that causes the film viewer region to emit light with high brightness. The film-diagnosis termination operation is performed by, for example, displaying a GUI component which receives an instruction on the medical image display apparatus 100 in a menu of a viewer application, and/or operating the GUI through the UI unit 101 by the user.

<Detailed Processing Flow of Film-Region-Determination Unit 107 and Film-Viewer-Region-Correction Unit 111>

Figure 6:
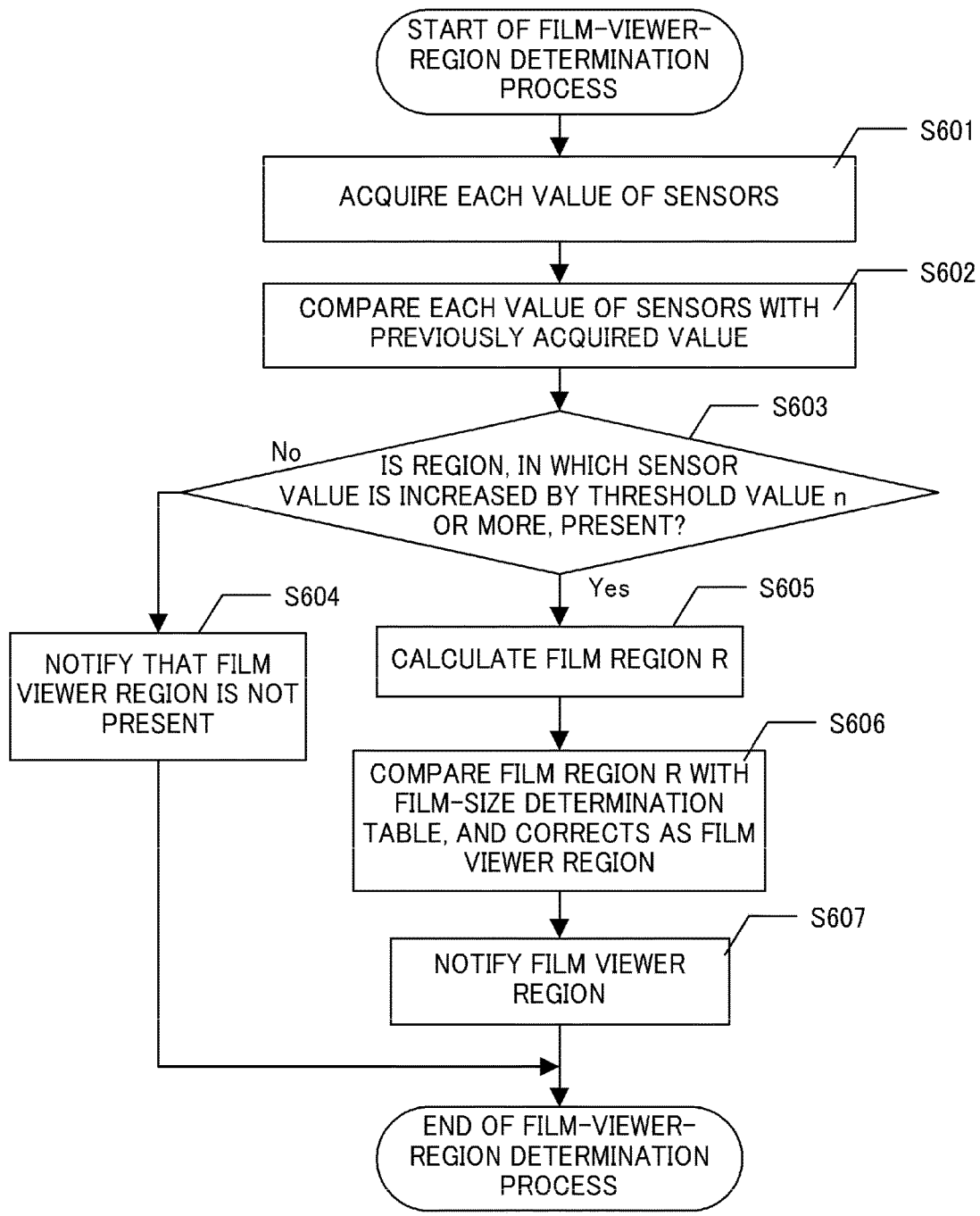
FIG. 6 is an operation flowchart of a film viewer region determination of the first embodiment.

FIG. 6 is a flow diagram representing a film-viewer-region-determination process in the film-region-determination unit 107 and the film-viewer-region-correction unit 111 in Step S406 of FIG. 4 described above.

In Step S601, the film-region determination unit 107 acquires each sensor value from the sensors 109 through the sensor-value-acquisition unit 108. These sensor values are second detection values that are detected by the above plurality of optical sensors in a state in which the above object to be observed is fixed on the screen.

In Step S602, the film-region-determination unit 107 calculates finite differences between the acquired sensor values and previously-acquired sensor values, and the process moves to Step S603. The previously-acquired sensor values are first detection values that are detected by the above plurality of optical sensors in a case in which the above object to be observed is not fixed on the screen.

Figure 7A:
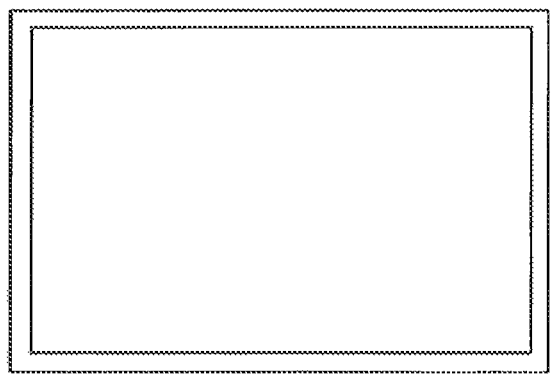
FIGS. 7A and 7B show screen examples of a state in which a film is not placed on the screen, according to first embodiment.
Figure 7B:
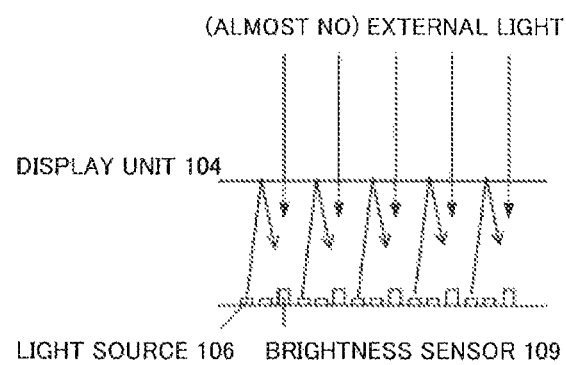

In a case in which the film is not placed on the medical image display apparatus as shown in FIG. 7A, each of the sensors 109 receives only light which is emitted from the corresponding BL 106 and reflected by the display unit 104 as shown in FIG. 7B (and potentially some external light, if there is any). Under dark environment conditions such as in a room for radiographic interpretation, the light-receiving quantity of each sensor 109 is not influenced by external light.

Figure 8A:
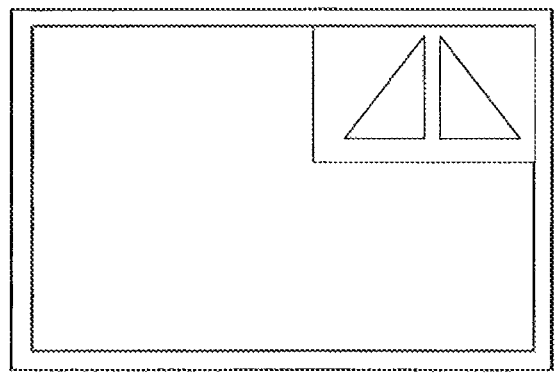
FIGS. 8A and 8B show screen examples of a state in which the film is placed on the screen according to the first embodiment.
Figure 8B:
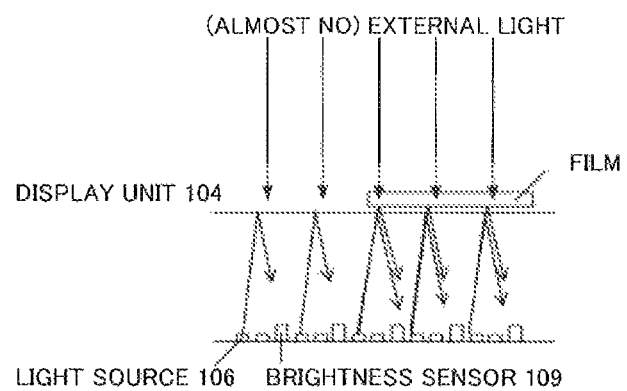

Additionally, in a state where the film is placed on the medical image display apparatus as shown in FIG. 8A, in a region on which the film has been placed, each sensor 109 receives both light which is reflected by the display unit 104, and light which is transmitted through the display unit 104 and reflected back to the sensors by the film. Therefore, as shown in FIG. 8B, the light-receiving quantity of each sensor 109 in the region on which the film has been placed is larger than the light-receiving quantity of each sensor 109 in the region where the film has not been placed. Accordingly, as to each of the sensor values of the sensors 109, a value obtained before the film is placed is subtracted from a value obtained after the film is placed, so that the film region can be identified. As an example, FIG. 9A shows the respective sensor values of the sensors 109 (with IDs from 1 to z via m, m+1 and n) obtained before the film is placed, and FIG. 9B shows the respective sensor values of the sensors 109 obtained after the film is placed.

In Step S603, the film-region-determination unit 107 determines whether or not each sensor value is increased by a threshold value or more (herein defined as a threshold value n) on the basis of the finite difference calculated in Step S602. In a case where no sensor 109 is present that has had its sensor value increased by the threshold value n or more, the film-region determination unit 107 notifies the control unit 103 that the film viewer region is not present in Step S604. In a case where a sensor 109 is present that has a sensor value that is increased by the threshold value n or more, the film-region determination unit 107 determines that there is a film fixed to the screen and performs the process of Step S605.

Figure 10:
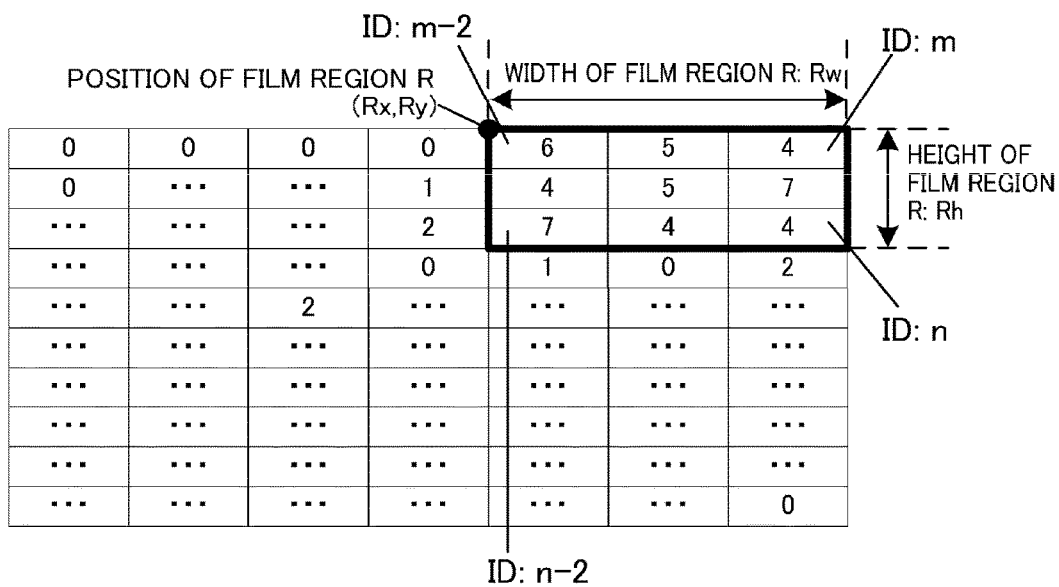
FIG. 10 shows Example 1 related to the correction of the film viewer region of the first embodiment.

In Step S605, from a positional relation of the sensors 109 having sensor values that are each increased by the threshold value n or more, the film-region determination unit 107 calculates a position (Rx, Ry) of a film region R (See FIG. 10). Additionally, the film-region determination unit 107 calculates the size (width Rw and height Rh) of the film region R based on a distance between the sensors (this distance is known as a sensor-fixing interval). In the medical image display apparatus 100, the positions and the fixing intervals of the sensors 109 are determined, and therefore the sensors 109 with sensor values increased by the threshold value n or more are identified, so that it is possible to calculate the position and the size of the film region R. FIG. 10 is a figure showing an example of finite difference values of the respective sensor values obtained before and after the fixing of the film, which are calculated from FIG. 9A and FIG. 9B, and the film region R that is calculated from the positional relation of the sensors 109 that have sensor values each increased by the threshold value n or more (where n is 3 in the present example). The film-region determination unit 107 notifies the film-viewer-region-correction unit 111 of the calculated position (Rx, Ry) and size (width Rw and height Rh) of the film region R through the control unit 103. In a case in which the size of the film region R is a predetermined value or less, it may be determined that the film viewer region is not present.

In Step S606, the film-viewer-region correction unit 111 extracts the size of a film closest to the received size (width Rw and height Rh) of the film region R, from the film-size determination table which is stored in the film-size-storage unit 110. Then, the film-viewer-region correction unit 111 corrects the size (width Fw and height Fh) of the film by determining a typical size that is closest to the size of the film region R calculated in Step S605 and setting this as the corrected size of the film region R.

In Step S607, the film-viewer-region-correction unit 111 notifies the control unit 103 of the position (Rx, Ry) of the film region R and the size (width Fw and height Fh) of the film region R obtained after the correction as information of the position and the size of the film viewer region. In a subsequent process, as described in S407, the control unit 103 notifies the BL-control unit 105 of this received information of the position and the size of the film viewer region. Then, the BL-control unit 105 allows the divided region of the BLs 106 corresponding to the film viewer region to emit light with higher brightness compared to other divided regions.

<Effects>

As described above, according to the first embodiment, a dedicated sensor such as a linear sensor and a touch panel are not needed, and it is possible to detect a film region with a simple circuit configuration at a low cost, and to set the film region as a film viewer region. Additionally, the reflected light of the BLs is utilized, so that also in a dark environment in which little light enters from the outside of the medical image display apparatus, like the room for radiograph interpretation, the film region can be detected to be set as the film viewer region.

Figure 11:
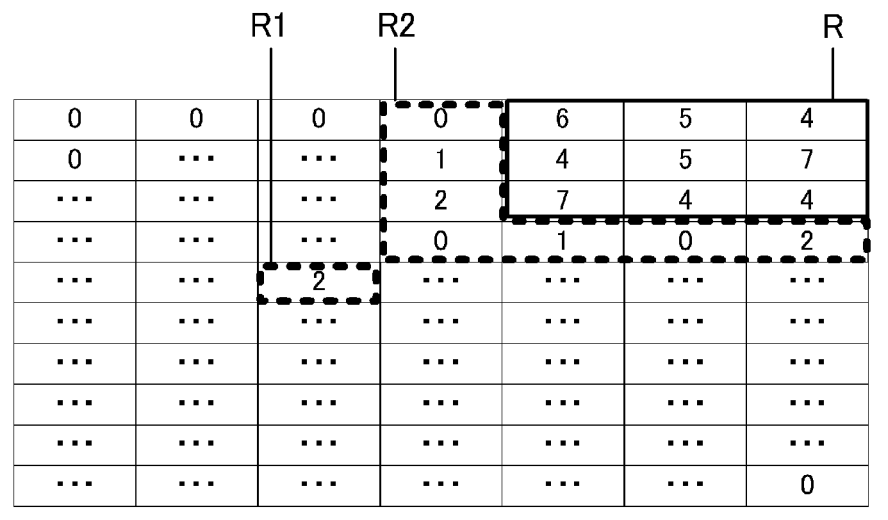

In the first embodiment, the film region is calculated by a single threshold value in Step S605. However, the determination of the film region may be made by a plurality of threshold values. For example, as shown in FIG. 11, a rectangular region R that includes sensors with sensor values that are each increased by a at least a threshold value 3 (or any other first threshold value) is defined as a primary region. Sensors adjacent the primary region are also analysed. If there are a number of sensors greater than a threshold number of sensors (the third threshold number) that have a sensor value change of at least a second threshold value (threshold value 2 in the present example, then the region containing that number of sensors is a secondary region R2. The film region is expanded to include both the primary region R1 and the secondary region R2. Additionally, even when a sensor having a sensor value which is increased by at least the second threshold value (here, of 2) is present in a region R1 which is not included in the region R2 adjacent to the primary region, the region R1 where the sensor is present is not determined as the film region. Thus, the film region is calculated by using both a plurality of threshold values and the relationship of the sensors with sensor values having those threshold values so that it is possible to reduce the influence of a measurement error by the noise of the sensors and to determine the film region accurately.

In the first embodiment, in Step S607, the position (Rx, Ry) of the sensor 109 located at the uppermost left position of the film region R is used as the defining position (Rx, Ry) of the film viewer region. The film region R after the correction (to include R2) may be calculated in such a way as to keep the center of the film region R in the same position even after the correction. In the first embodiment, the first BL control mode and the second BL control mode are switched periodically However, the setting and the releasing of the film viewer region may be performed by the designation of the BL control mode from the menu or the like by the user, thus independently of the periodic switching of the BL control modes.

Second Embodiment

Figure 12:
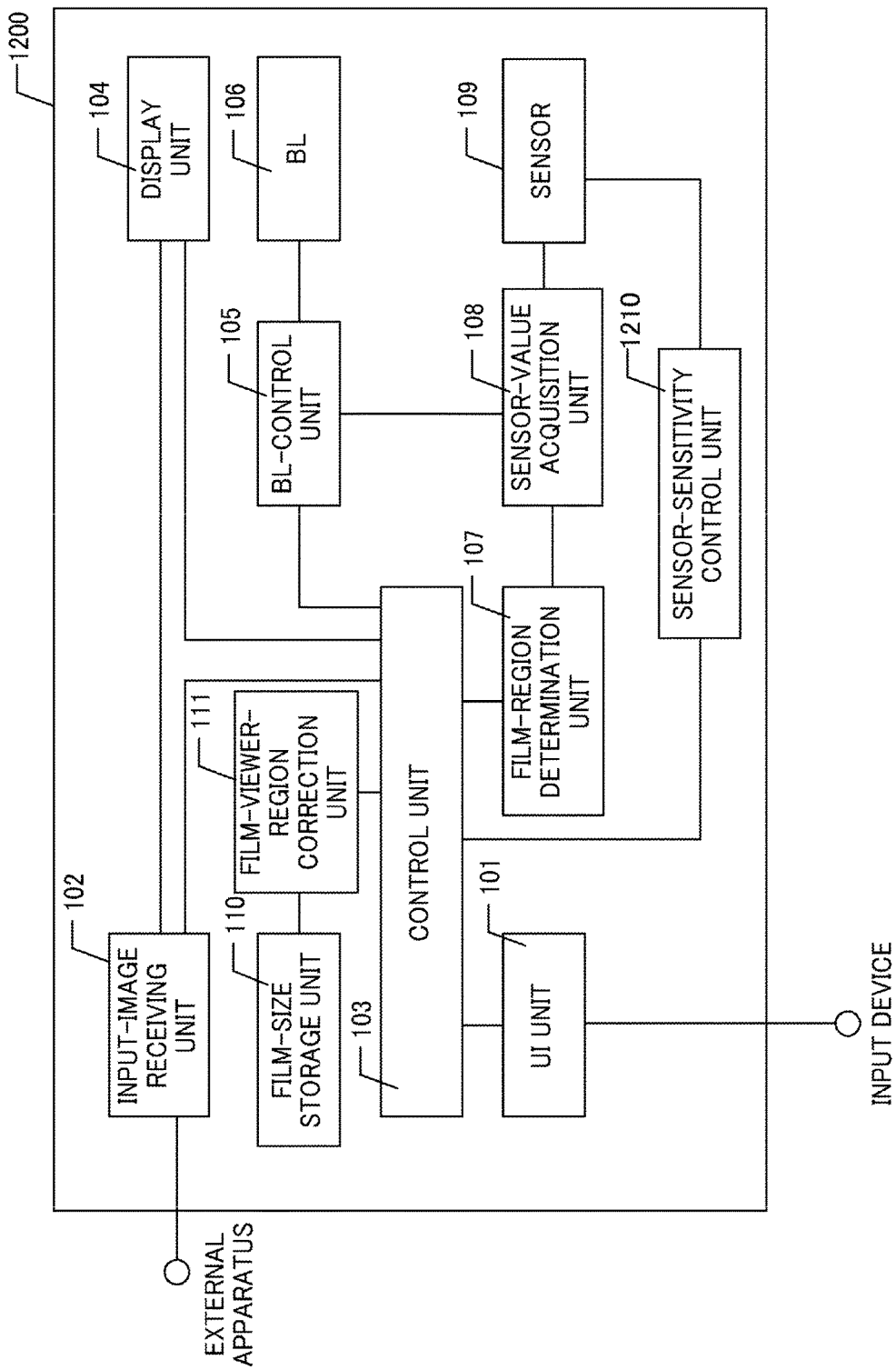
FIG. 12 is a block diagram showing a configuration of a medical image display apparatus of a second embodiment.

In a second embodiment of the present invention, an example will be described in which the sensitivity of optical sensors at the time of the execution of a second BL control mode is made to be lower than the sensitivity of the optical sensors at other times in order to determine a film region. Configurations identical with those of the first embodiment will be omitted. FIG. 12 is a block diagram showing a configuration of a medical image display apparatus 1200 according to the second embodiment. The second embodiment is different from the first embodiment in that a sensor-sensitivity control unit 1210 is added, and a process performed by the control unit 103 is different.

Figure 13:
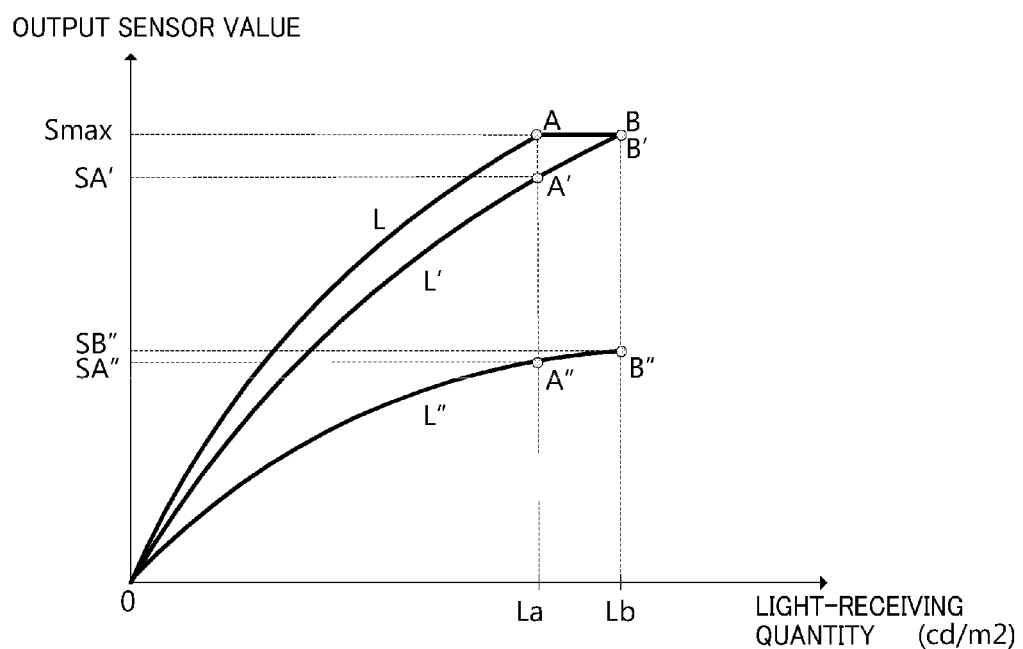
FIG. 13 is a relation diagram of the light-receiving quantity of sensors and sensor values according to the second embodiment.

In a case where the sensor-sensitivity control unit 1210 is notified from the control unit 103 that the second BL control mode is started, the sensitivity of sensors 109 corresponding to a film region is made lower so that sensor values of the sensors 109 corresponding to a film region are not saturated. FIG. 13 is a figure illustrating the relation between the amount of light received (denoted in FIG. 13 as the light-receiving quantity) by the sensors 109 and a corresponding sensor value. In FIG. 13, the light-receiving quantity of the sensors 109 located in the film region is denoted by Lb, and the light-receiving quantity of sensors 109 located outside the film region is denoted by La. A curve L is a sensor sensitivity curve, and the sensor sensitivity curve becomes L' or L" by lowering sensitivity. For example, in a case where the sensor sensitivity curve is L, at the light-receiving quantity La of the sensors 109 located outside the film region (B) and the light-receiving quantity Lb of the sensors 109 located in the film region (A), both output sensor values (A and B) become Smax, and are the same, and therefore it is impossible to perform determination of the difference between the two values and it is impossible to determine the film region (this is known as the saturation state). On the other hand, when the sensor sensitivity is excessively lowered to become sensor sensitivity curve L", the respective output sensor values of the light-receiving quantities La and Lb at points A" and B" become SA" and SB", the difference between them is excessively reduced, and the determination as to the film region also becomes difficult. Therefore, in the second embodiment, the sensor sensitivity is adjusted between these two extremes such that the determination of the film region can be most accurately performed.

<Detailed Whole Processing Flow>

Figure 14:
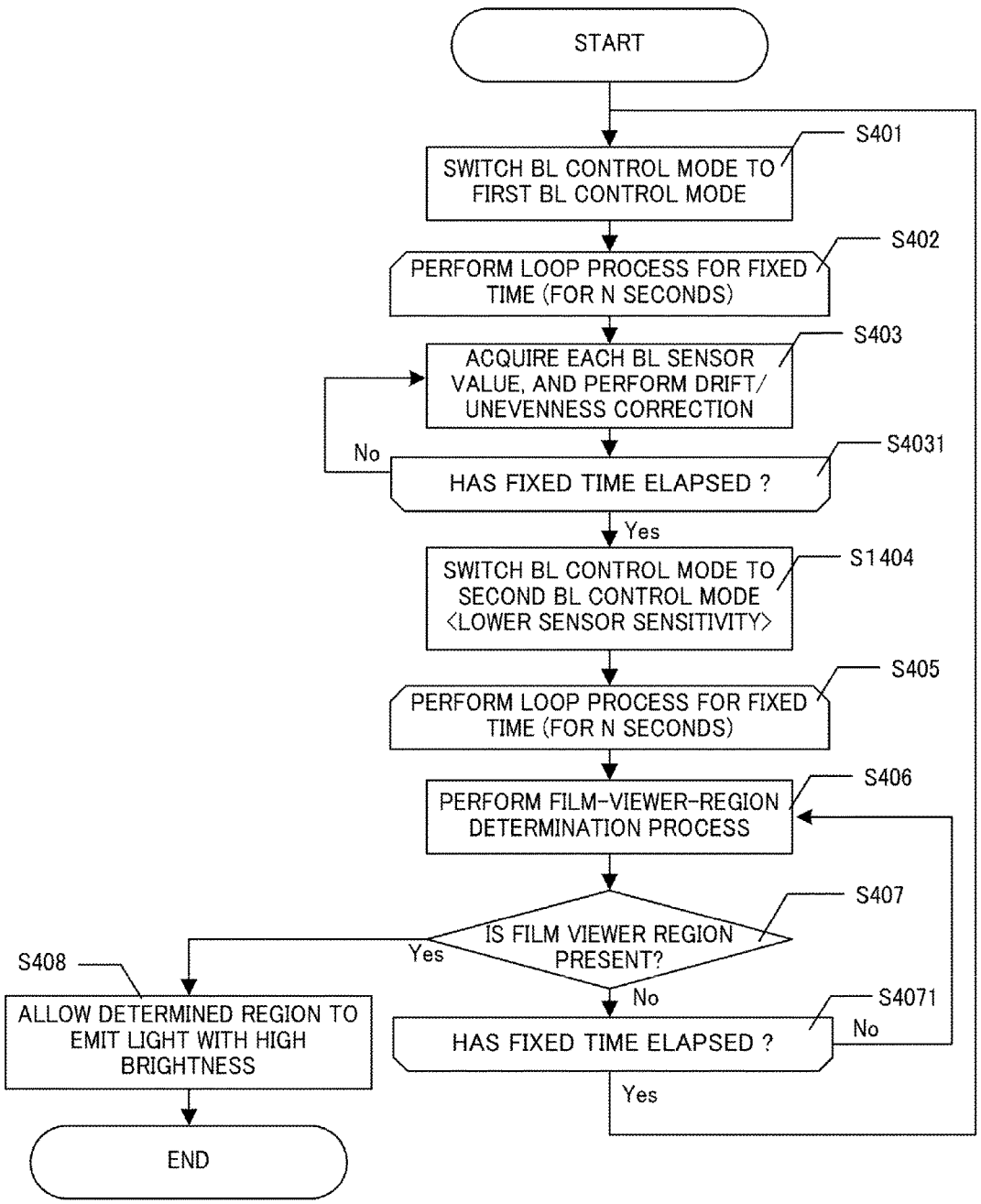
FIG. 14 is an operation flowchart of the medical image display apparatus of the second embodiment.

FIG. 14 is a flow diagram showing whole processes according to the second embodiment. The difference between the second embodiment and the first embodiment is Step S1404. In Step S1404, the control unit 103 notifies a BL-control unit 105 to change the BL control mode to the second BL control mode, and acquires current BL-light-emission quantity of BLs from the BL-control unit 105. Then, the control unit 103 notifies the sensor-sensitivity control unit 1210 of information on sensor sensitivity including a sensor value of each sensor 109 corresponding to the film region that is not saturated with the current BL-light-emission quantity. The sensor-sensitivity control unit 1210 lowers the sensitivity of each sensor 109 to the notified sensor sensitivity in order to avoid sensor saturation.

The light-receiving quantity of sensors 109 in the film region is calculated as the sum of the light-receiving quantity of the sensors 109 located outside the film region and the quantity of light that is transmitted through the display unit 104 and reflected by the film. Additionally, the quantity of the light reflected by the film can be calculated from the reflectance of the film, the transmittance of the display unit 104, and the amount of light emitted ("light-emission quantity) from the BLs 106. Therefore, the control unit 103 holds information of sensor sensitivity at which each sensor 109 is not saturated in a table, the information being previously determined for each BL light-emission quantity. Alternatively, a table is previously stored in a storage apparatus (not shown), and the control unit 103 reads the table from the storage apparatus. Yet alternatively, sensor sensitivity with which the film region is easily identified may be previously measured by an experiment and determined, and this information may be held in a table.

<Effects>

As described above, at the time of the execution of the second BL control mode, the sensitivity of the sensors is lowered in a sensor range in which the film region can be determined, and determination is performed so that it is possible to suppress the saturation of the sensor values in the film region in order to detect the film region accurately. In the second embodiment, every time the second BL control mode is executed, the light-receiving quantity in the film region may be calculated by using the light-receiving quantity of the sensors 109 as the light-receiving quantity of the outside of the film region, and sensor sensitivity may be lowered so that the sensor values are not saturated. In the second embodiment, sensor sensitivity is lowered so that the sensor values are not saturated. However, in a case where the BL-light-emission quantity is small at the time of the execution of the second BL control mode, and the film region is difficult to determine, the light-emission quantity of the BLs may be increased.

Third Embodiment

In a third embodiment of the present invention, at the time of the execution of a second BL control mode, BLs are turned on (and off) one by one so that each sensor is not influenced by the emission of other BLs. Additionally, a method of determining the film region by increasing sensor sensitivity so as to increase a difference between sensor values in a film region and sensor values in a region other than the film region will be described. A configuration of a medical image display apparatus 1200 is the same as that of the second embodiment, but processes performed by the control unit 103, the BL-control unit 105, the film-region determination unit 107, and the sensor-sensitivity control unit 1210 of this embodiment is different from those of the second embodiment. Description of parts identical with those of the second embodiment will be omitted.

<Detailed Flow in Second BL Control Mode>

Figure 15:
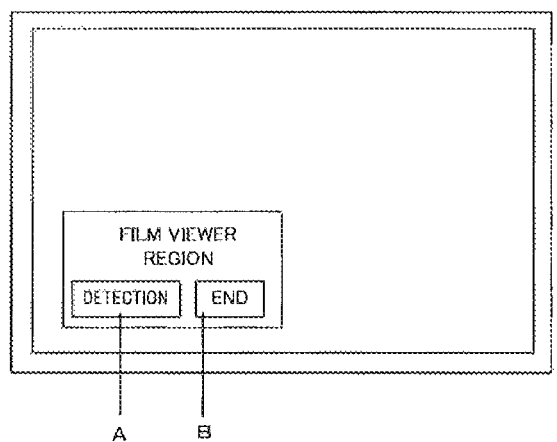
FIG. 15 is a GUI display example of a third embodiment.

FIG. 15 is a GUI display example in a case where a user performs menu display by using a UI unit 101. A menu includes a detection button A and an end button B. In a case where the user selects the detection button A, the medical image display apparatus 1200 identifies a region where a film is placed, and causes BLs 106 to emit light with high brightness as a film viewer region. In a case where the end button B is selected, the medical image display apparatus 1200 terminates a state where the BLs 106 emit light with high brightness.

Figure 16:
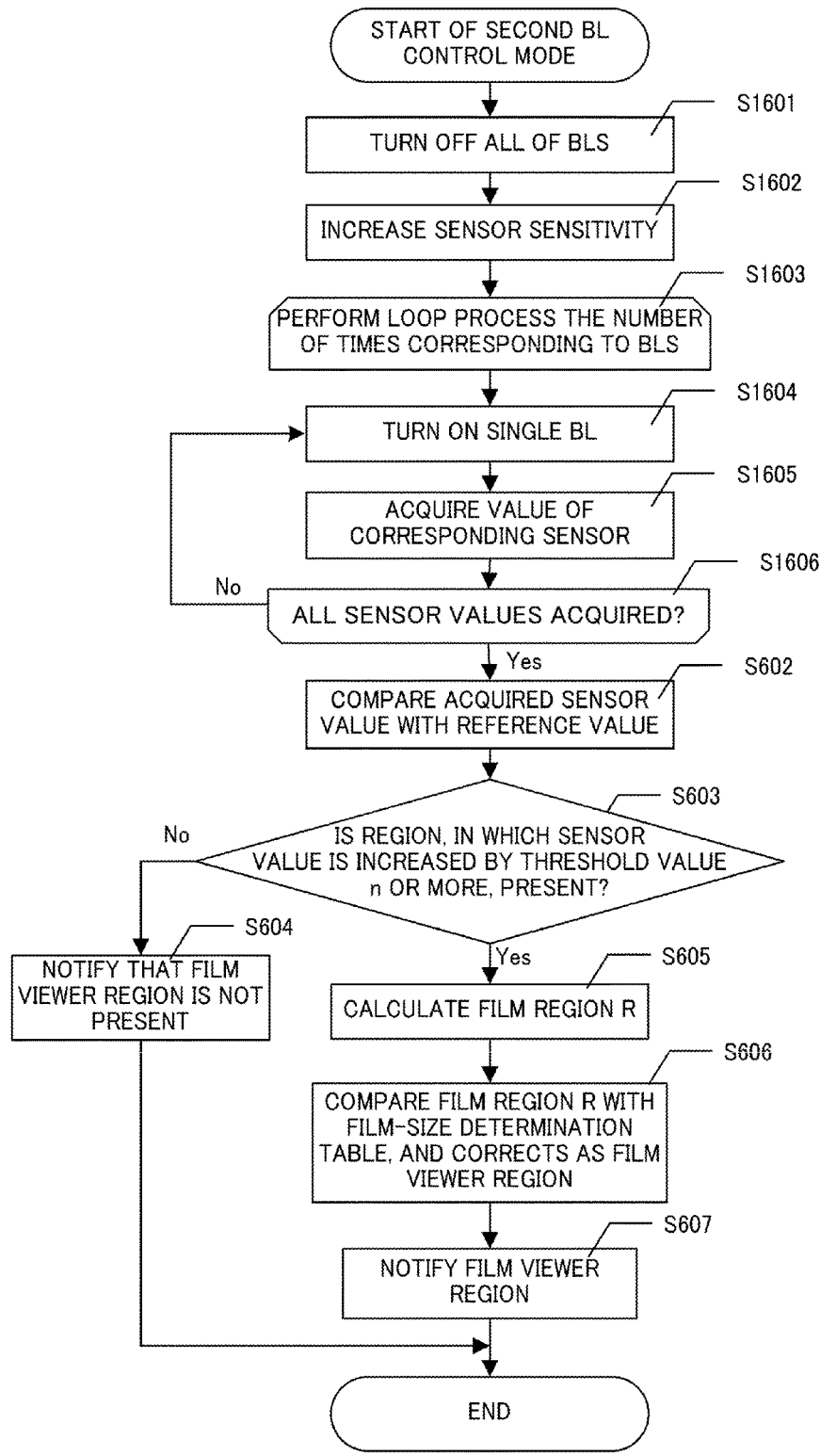
FIG. 16 is an operation flow of film viewer region determination of the third embodiment.

FIG. 16 is a detailed flow at the time of the execution of the second BL control mode, according to the third embodiment. This flow is started when the user selects the detection button A in FIG. 15 described above.

In Step S1601, the control unit 103 notifies the BL-control unit 105 to change the BL control mode to the second BL control mode. The BL-control unit 105 turns off all of the BLs 106 when the second BL control mode is started.

Figure 17:
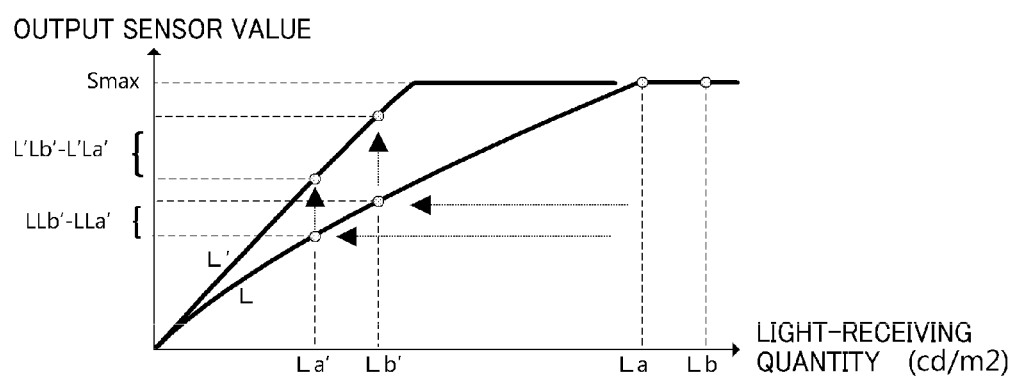
FIG. 17 is a relation diagram of the light-receiving quantity of sensors and sensor sensitivity according to the third embodiment.

In Step S1602, after performing the process of S1601, the control unit 103 notifies the sensor-sensitivity control unit 1210 that the second BL control mode is started. The sensor-sensitivity control unit 1210 increases the sensor sensitivity of sensors 109. FIG. 17 is a figure showing an example of relation between the light-receiving quantity of the sensors 109 and an output sensor value. In FIG. 17, the light-receiving quantity of the sensors 109 located in the film region is denoted by Lb', and the light-receiving quantity of sensors 109 located outside the film region is denoted by La'. The curve L is a sensor sensitivity curve, and becomes a sensor sensitivity curve L' when sensitivity of the sensor is increased. Herein, a difference between output sensor values corresponding to the light-receiving quantity La' of the sensors 109 located outside the film region and output sensor values corresponding to the light-receiving quantity Lb' of the sensors 109 located in the film region in the case of the sensor sensitivity curve L is denoted by LLb'-LLa'. By comparison, in a case where the difference between the output sensor values corresponding to the light-receiving quantity La' of the sensors 109 located outside the film region and the output sensor values corresponding to the light-receiving quantity Lb' of the sensors 109 located in the film region is denoted by L' Lb'-L' La' in a case where the sensor sensitivity is increased to give the sensor sensitivity curve L'. As shown in the figure, the sensors 109 are likely to be saturated by increasing the sensor sensitivity. However, a finite difference between the output sensor values inside and outside the film region is increased, and therefore the film region is easily determined. Therefore, the relation between the light-emission quantity of the BLs and sensor sensitivity with which the film region is easily determined, is previously measured by an experiment and determined, and this information is held in the control unit 103 or in an external storage apparatus.

In Step S1603, the control unit 103 performs the processes of S1604 and S1605, which will be described later, as a loop, the number of times the steps are performed corresponding to the number of the BLs. In a case where the processes are performed the number of times corresponding to the number of the BLs (Yes in S1606), the process moves to a process of S602 and subsequent processes.

Figure 18B:
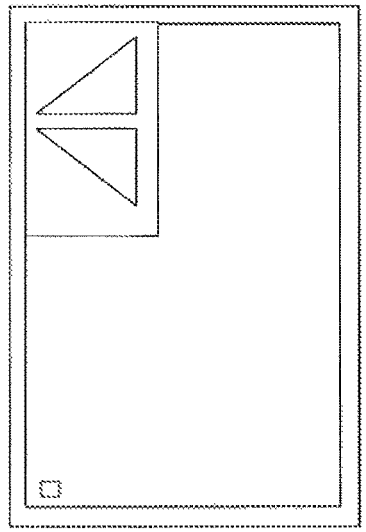
FIGS. 18A to 18C are figures showing lighting examples of backlights of the third embodiment.
Figure 18A:
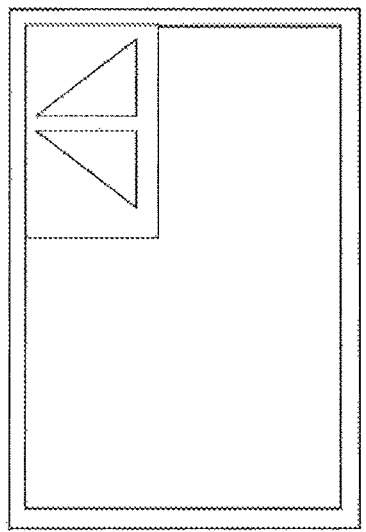
Figure 18C:
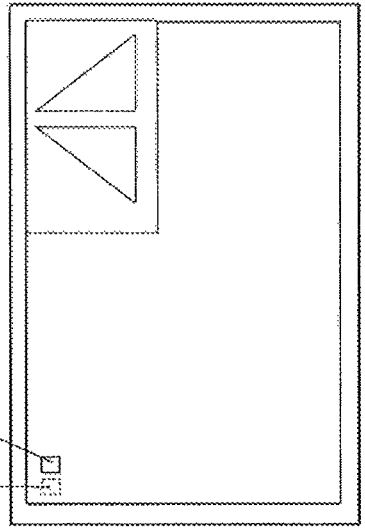

In Step S1604, the control unit 103 notifies the BL-control unit 105 of a BL 106 to be caused to emit light. The BL-control unit 105 causes the notified single BL 106 to emit light. The light-emission quantity of the BL 106 at this time is determined by reading an optimum value which is previously measured by an experiment to be obtained as described above, from the storage apparatus. FIG. 18 is a figure showing case where the BLs are caused to emit light individually. FIG. 18A shows a state where all of the BLs are turned off, and FIG. 18B shows a state where the BL-control unit 105 causes the single BL 106 to emit light. Then, when the BL-control unit 105 is notified of a BL 106 to be caused to emit light next time, from the control unit 103, the BL-control unit 105 turns off the BL which is turned on last time, and turns on the notified BL 106.

In Step S1605, after the emission of the BL 106 is completed in S1604, the control unit 103 designates ID of a sensor, the sensor value of which is to be acquired, to the film-region determination unit 107. The film-region determination unit 107 acquires and holds the sensor value of the sensor of the designated sensor ID, through the sensor-value acquisition unit 108.

<Effects>

As described above, the BLs are caused to emit light individually, so that it is possible to reduce the influence on the sensors by the emission of other BLs. Additionally, in a case where the light-receiving quantity of the sensors is lowered by the individual emission of the BLs, distinction between a region where the film is placed, and a region where the film is not placed can be easily performed by increasing sensor sensitivity, and it is possible to improve the accuracy of the film viewer region. In the third embodiment, the BLs are caused to emit light individually, so that the quantity of light reaching the sensors is lowered, and therefore the sensitivity of the sensors is increased. However, sensor sensitivity may be increased, in a case where the quantity of the light received by the sensors is lowered by lowering the amount of light emitted (the light-emission quantity) of all of the BLs. Alternatively, the sensor sensitivity may not be adjusted, and the light-receiving quantity of the sensors may be secured by increasing the light quantity of the BLs which are to be caused to individually emit light. In the third embodiment, the respective BLs are individually turned on for one time each. However, the processes of FIG. 16 may be repeatedly performed a plurality of times, and a process of identifying the film viewer region may be repeatedly performed. Consequently, even in a case where the user places the film in the medical image display apparatus after instructing the detection start of the film viewer region, or even in a case where the position of the film is adjusted after the film is placed, it is possible to identify the film region accurately.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-026811, filed on Feb. 14, 2014, which is hereby incorporated by reference herein in its entirety.

What is claimed is:
1. An image-display apparatus comprising:
a display screen;
a plurality of light-emitting units arranged to emit light behind a rear surface of the display screen;
a plurality of light sensors provided at different positions behind the rear surface of the display screen to detect light including light emitted from at least one light-emitting unit and light reflected from an object placed on a front surface of the display screen, and to output at least a first detection value at a first time and a second detection value at a second time; and
a determination unit configured to determine, based on a difference between the first and second detection values output by the plurality of light sensors, a position of an object region of the display screen on which the object is placed, wherein
a GUI (Graphical User Interface) image including a menu, which receives an instruction from a user, is displayed on the display screen, and
light emitted from at least one light-emitting unit is irradiated to the object on the display screen.
2. An image-display apparatus according to claim 1, wherein
the determination unit is configured to calculate the difference between the first and second detection values for each light sensor and to determine that a region of the display screen corresponding to a light sensor for which the difference between the first and second detection values is greater than a first threshold is the object region.
3. The image-display apparatus according to claim 1, further comprising:
a control unit configured to cause light-emitting units arranged in the object region to emit light with greater brightness than light-emitting units arranged outside of the object region.
4. The image-display apparatus according to claim 1, wherein
the determination unit is configured to determine, as the object region:
a primary region in which at least one light sensor outputs a first detection value and a second detection value between which a difference is at least a first threshold value, and
a secondary region that is located adjacent to the primary region and in which each of a number of light sensors, the number being at least a third threshold number of light sensors, outputs a first detection value and a second detection value between which a difference is at least a second threshold value.
5. The image-display apparatus according to claim 1, wherein
the determination unit is configured to determine that an object is not placed on the display screen in a case where no light sensor is present for which a difference between the first detection value and the second detection value is a threshold value or more.
6. The image-display apparatus according to claim 1, further comprising an acquisition unit configured to acquire typical values of a size of the object, wherein
the determination unit is configured to correct the detected object region on the basis of a typical value closest to a size of the determined object region from among the typical values acquired by the acquisition unit.
7. The image-display apparatus according to claim 1, wherein
the control unit is configured to display a black image in a region of the display screen corresponding to a part that is not included in the object region.
8. The image-display apparatus according to claim 1, wherein
the control unit is configured to make the light sensitivity of the light sensors lower when the determination unit determines that the object region exists than when the determination unit determines that the object region does not exist.
9. The image-display apparatus according to claim 1, wherein
the control unit is configured to optimise the light sensitivity of the light sensors so that the light sensors do not experience light saturation either in an object region nor in a region outside the object region, and so that the first and second detection values are distinguishable between the object region and the region outside the object region.
10. The image-display apparatus according to claim 1, wherein
the determination unit is configured to acquire, for each of the plurality of light sensors, the first detection value which is a detection value output when the image-display apparatus does not have the object placed on it and the second detection value which is a detection value output when the image-display apparatus does have an object placed on it, and to determine the position of the object region on the basis of the difference between the first detection value and the second detection value.
11. The image-display apparatus according to claim 1, wherein
the object is a film.

12. The image-display apparatus according to claim 11, wherein the GUI image includes a menu for starting an image diagnosis of the film or a menu for terminating the image diagnosis of the film.

13. A control method for an image-display apparatus, the image-display apparatus comprising:
   a display screen;
   a plurality of light-emitting units arranged to emit light behind a rear surface of the display screen; and
   a plurality of light sensors provided at different positions behind the rear surface of the display screen to detect light including light emitted from at least one light-emitting unit and light reflected from an object placed on a front surface of the display screen, and to output at least a first detection value at a first time and a second detection value at a second time,
   the control method comprising:
   lighting the display screen with at least one light-emitting unit;
   detecting light received by the plurality of light sensors;
   each light sensor outputting a first detection value when the image-display apparatus does not have an object placed on it and a second detection value when the image-display apparatus does have an object placed on it;
   receiving detection values from each light sensor;
   determining a position of an object region of the display screen on which the object is placed on the basis of a difference between the first and second detection values output from the plurality of light sensors; and
   causing at least one light-emitting unit in the object region to emit light with a greater brightness than other regions, wherein
   a GUI (Graphical User Interface) image including a menu, which receives an instruction from a user, is displayed on the display screen, and
   light emitted from at least one light-emitting unit is irradiated to the object on the display screen.

14. An image-display apparatus comprising:
   a display screen;
   a plurality of light-emitting units arranged to emit light behind a rear surface of the display screen;
   a plurality of light sensors provided at different positions behind the rear surface of the display screen to detect light emitted from at least one light-emitting unit and light reflected from an object placed on a front surface of the display screen, and to output at least a first detection value and a second detection value;
   a determination unit configured to determine, based on a difference between the first and second detection values output by the plurality of light sensors, a position of an object region of the display screen on which the object is placed; and
   a control unit configured to cause light-emitting units arranged in the object region to emit light with greater brightness than light-emitting units arranged outside of the object region, wherein
   a GUI (Graphical User Interface) image including a menu, which receives an instruction from a user, is displayed on the display screen.

15. The image-display apparatus according to claim 14, further comprising an acquisition unit configured to acquire typical values of a size of the object, wherein
   the determination unit is configured to correct the detected object region on the basis of a typical value closest to a size of the determined object region from among the typical values acquired by the acquisition unit.

16. The image-display apparatus according to claim 14, wherein
   the control unit is configured to display a black image in a region of the display screen corresponding to a part that is not included in the object region.

17. The image-display apparatus according to claim 14, wherein
   the object is a film.

18. The image-display apparatus according to claim 17 wherein the GUI image includes a menu for starting an image diagnosis of the film or a menu for terminating the image diagnosis of the film.

19. A control method for an image-display apparatus, the image-display apparatus comprising:
   a display screen;
   a plurality of light-emitting units arranged to emit light behind a rear surface of the display screen; and
   a plurality of light sensors provided at different positions behind the rear surface of the display screen to detect light emitted from at least one light-emitting unit and light reflected from an object placed on a front surface of the display screen, and to output at least a first detection value and a second detection value,
   the control method comprising:
   lighting the display screen with at least one light-emitting, unit;
   detecting light received by the plurality of light sensors;
   receiving, detection values from each light sensor;
   determining a position of an object region of the display screen on which the object is placed on the basis of a difference between the first and second detection values output from the plurality of light sensors; and
   causing light-emitting units arranged in the object region to emit light with greater brightness than light-emitting units arranged outside of the object region, wherein
   a GUI (Graphical User Interface) image including a menu, which receives an instruction from a user, is displayed on the display screen.

* * * * *